US010765853B2

(12) United States Patent
Neff et al.

(10) Patent No.: US 10,765,853 B2
(45) Date of Patent: Sep. 8, 2020

(54) HEMOSTATIC VALVE SYSTEM

(71) Applicant: Cook Medical Technologies LLC, Bloomington, IN (US)

(72) Inventors: Gary Neff, Bloomington, IN (US); William Gibbons, Bloomington, IN (US); Ram H. Paul, Jr., Bloomington, IN (US)

(73) Assignee: Cook Medicai Technologies LLC, Bloomington, IN (US)

(*) Notice: Subject to any disclaimer, the term of this patent is extended or adjusted under 35 U.S.C. 154(b) by 693 days.

(21) Appl. No.: 14/976,172

(22) Filed: Dec. 21, 2015

(65) Prior Publication Data
US 2016/0175576 A1 Jun. 23, 2016

Related U.S. Application Data

(60) Provisional application No. 62/095,272, filed on Dec. 22, 2014.

(51) Int. Cl.
A61M 39/06 (2006.01)
(52) U.S. Cl.
CPC ........ A61M 39/0613 (2013.01); A61M 39/06 (2013.01); A61M 2039/062 (2013.01);
(Continued)
(58) Field of Classification Search
CPC .............. A61M 39/0613; A61M 39/06; A61M 2039/062; A61M 2039/0626;
(Continued)

(56) References Cited

U.S. PATENT DOCUMENTS 4,436,519 A 3/1984 O'Neill
4,946,133 A 8/1990 Johnson et al.
(Continued)

FOREIGN PATENT DOCUMENTS

EP 2745896 A2 6/2014
FR 2 976 814 6/2011
(Continued)

OTHER PUBLICATIONS

English translation of WO2009118417. Obtained from Google Patents Oct. 5, 2018.*
(Continued)

Primary Examiner — Kevin C Sirmons
Assistant Examiner — Alexandra Lalonde
(74) Attorney, Agent, or Firm — Brinks Gilson & Lione

(57) ABSTRACT

A hemostatic valve assembly is disclosed. The assembly comprises a housing having a sidewall that tapers radially inwardly towards the housing distal end. A valve member having an open proximal end and a tapered distal end with an orifice formed therein is disposed within the housing chamber. The valve member is deformable between a closed configuration in which the orifice is substantially closed and an open configuration in which the orifice is open. A biasing member disposed proximal to the valve member is moveable between a longitudinally compressed condition and a longitudinally expanded condition. When in an expanded condition, the biasing member pushes the valve member longitudinally and against the tapered sidewall of the housing. The tapered sidewall of the housing urges the distal end of the valve member radially inwardly, thus urging the orifice to the substantially closed configuration.

22 Claims, 9 Drawing Sheets

(52) U.S. Cl.
CPC ............... *A61M 2039/0626* (2013.01); *A61M 2039/0673* (2013.01)

(58) Field of Classification Search
CPC .. A61M 2039/0673; A61M 2039/0646; A61M 2039/064; A61M 39/0693; A61M 39/045; A61M 39/26; A61M 39/22; A61M 2039/0666; A61M 2039/0653; A61M 2039/0633; A61M 2039/267; A61M 2039/2426; A61M 2039/066; A61M 39/04
See application file for complete search history.

(56) References Cited

U.S. PATENT DOCUMENTS

| | | |
|---|---|---|
| 5,195,980 A | 3/1993 | Catlin |
| 5,387,235 A | 2/1995 | Chuter |
| 5,456,713 A | 10/1995 | Chuter |
| 5,514,109 A | 5/1996 | Mollenauer et al. |
| 5,520,655 A | 5/1996 | Davila et al. |
| 5,520,666 A * | 5/1996 | Choudhury ......... A61M 39/045 604/537 |
| 5,664,939 A | 9/1997 | Giordani et al. |
| 5,720,776 A | 2/1998 | Chuter et al. |
| 5,727,770 A | 3/1998 | Dennis |
| 5,779,732 A | 7/1998 | Amundson |
| 5,895,376 A | 4/1999 | Schwartz et al. |
| 5,921,968 A * | 7/1999 | Lampropoulos .. A61M 39/0613 604/167.05 |
| 6,066,117 A | 5/2000 | Fox et al. |
| 6,089,541 A * | 7/2000 | Weinheimer .......... A61M 39/26 251/149.1 |
| 6,113,068 A * | 9/2000 | Ryan ................... A61M 39/045 251/149.4 |
| 6,331,176 B1 | 12/2001 | Becker et al. |
| 6,390,120 B1 | 5/2002 | Guala |
| 6,520,939 B2 | 2/2003 | Lafontaine |
| 6,942,691 B1 | 9/2005 | Chuter |
| 7,296,782 B2 | 11/2007 | Enerson et al. |
| 7,444,990 B1 | 11/2008 | Fisher |
| 8,011,363 B2 | 9/2011 | Johnson |
| 8,297,318 B2 | 10/2012 | Johnson |
| 2012/0316536 A1 * | 12/2012 | Carrez ............... A61M 39/1011 604/535 |
| 2013/0324975 A1 | 12/2013 | Douglas et al. |
| 2014/0018621 A1 | 1/2014 | Stout |
| 2014/0207083 A1 | 7/2014 | Pessin |
| 2014/0276462 A1 * | 9/2014 | Vincent ............. A61M 25/0097 604/256 |

FOREIGN PATENT DOCUMENTS

| | | | |
|---|---|---|---|
| WO | WO 94/14497 | 7/1994 | |
| WO | WO 2008/02285 A2 | 4/2008 | |
| WO | WO 2008042285 A2 * | 4/2008 | ........ A61M 25/0606 |
| WO | WO-2009118417 A1 * | 10/2009 | ............ A61M 39/04 |
| WO | WO 2013/115221 A1 | 8/2013 | |

OTHER PUBLICATIONS

Extended Search Report for related EPO Application No. 15275271.3-1662 dated Feb. 12, 2016 (7 pgs).

* cited by examiner

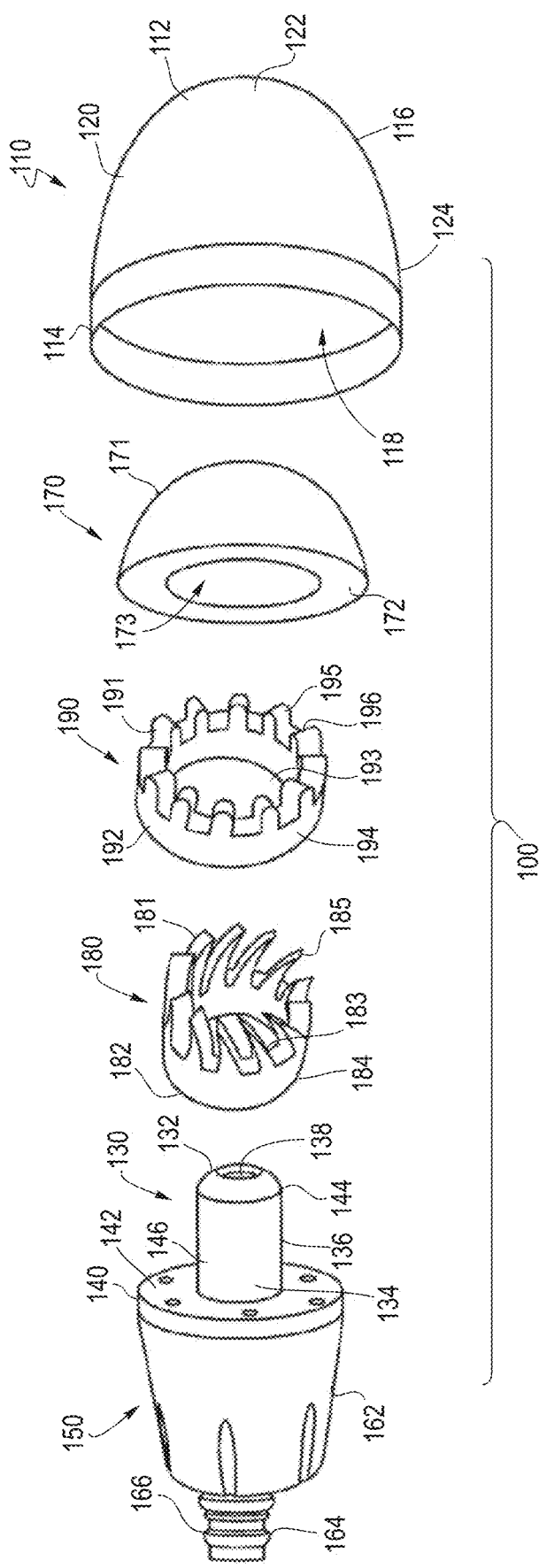

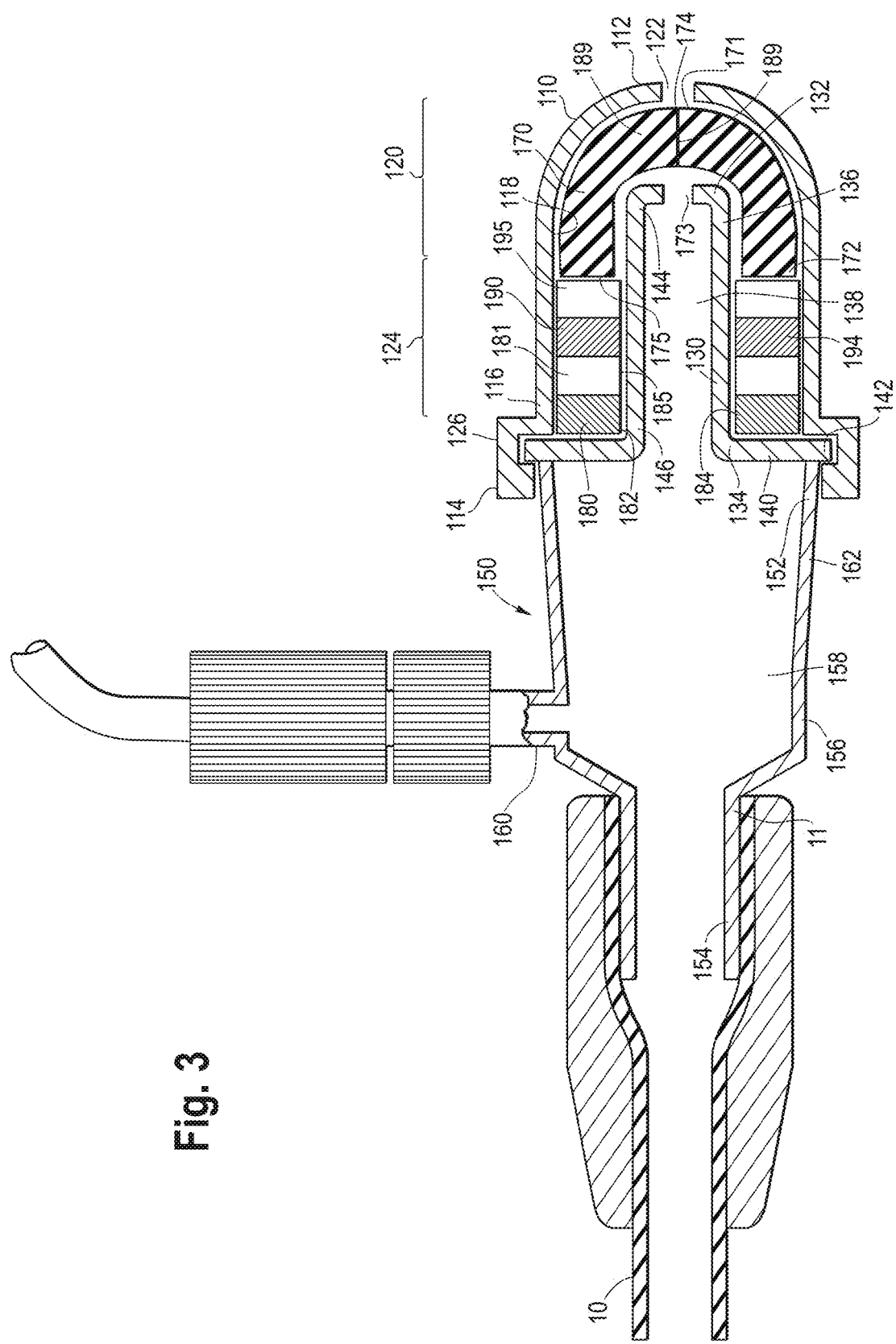

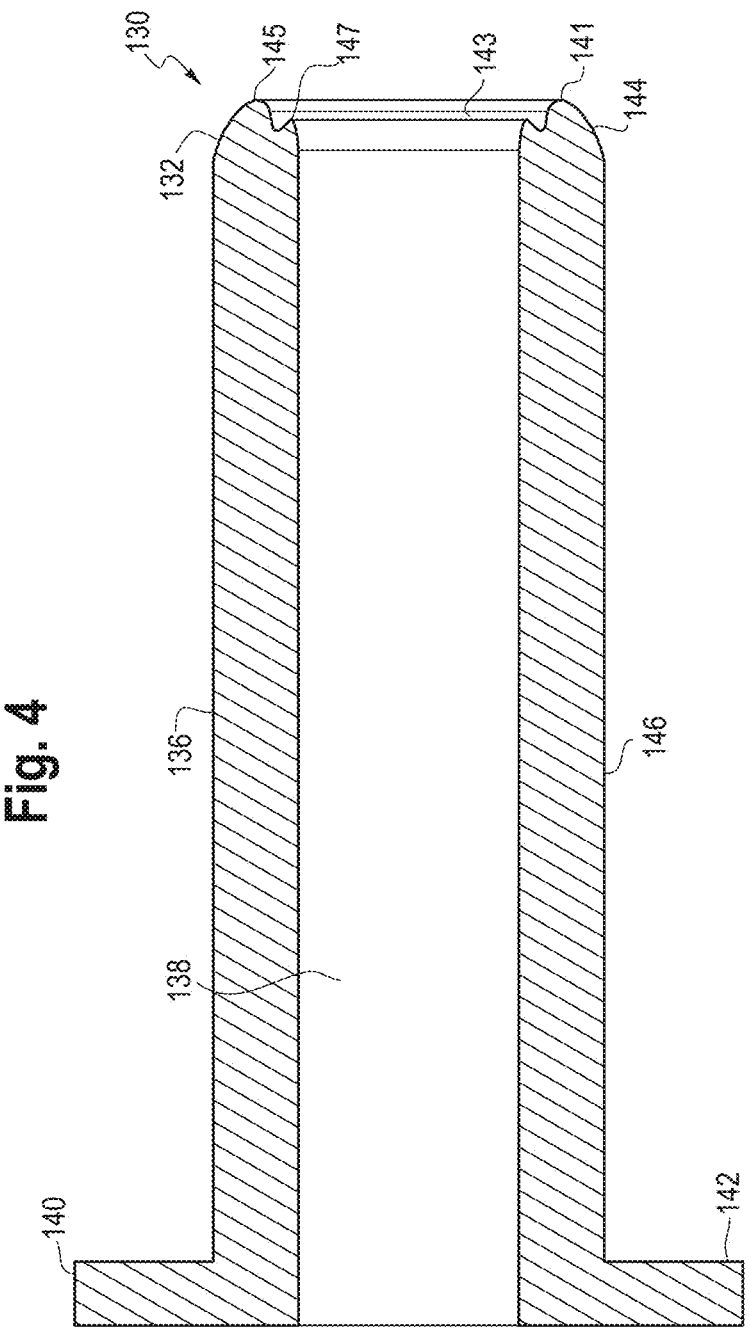

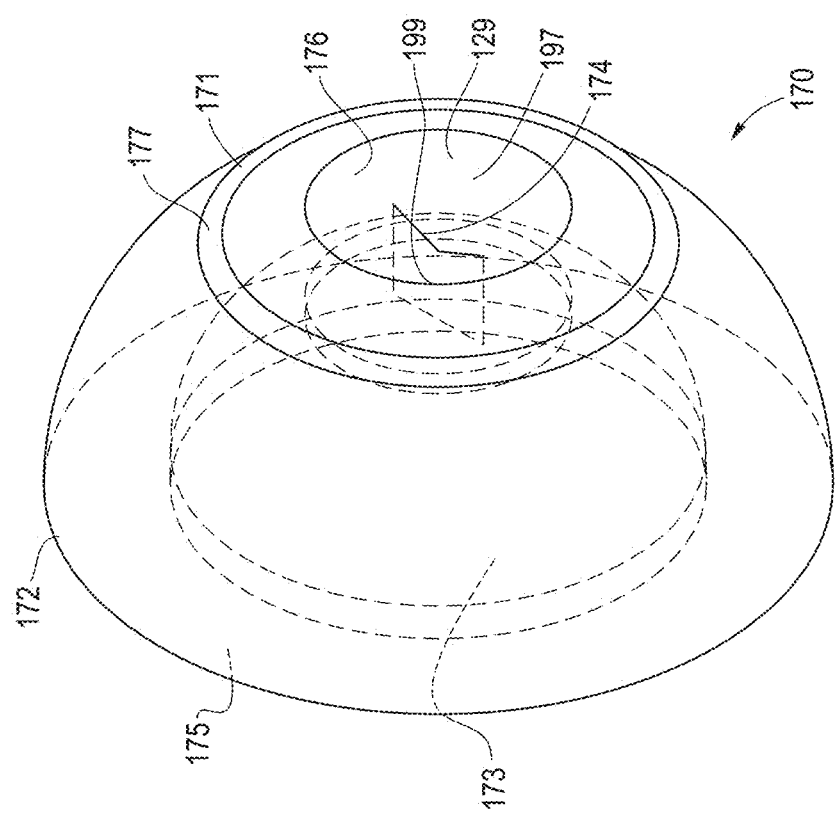

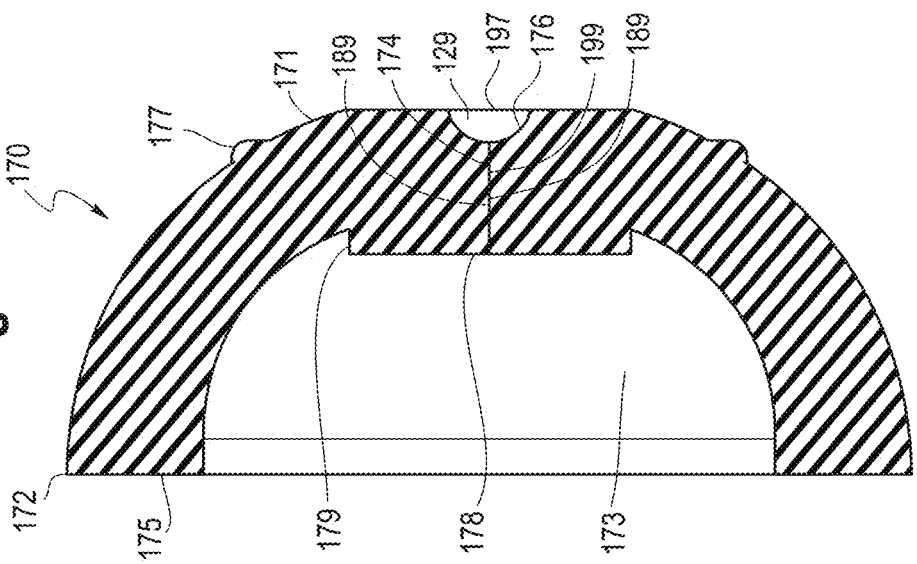
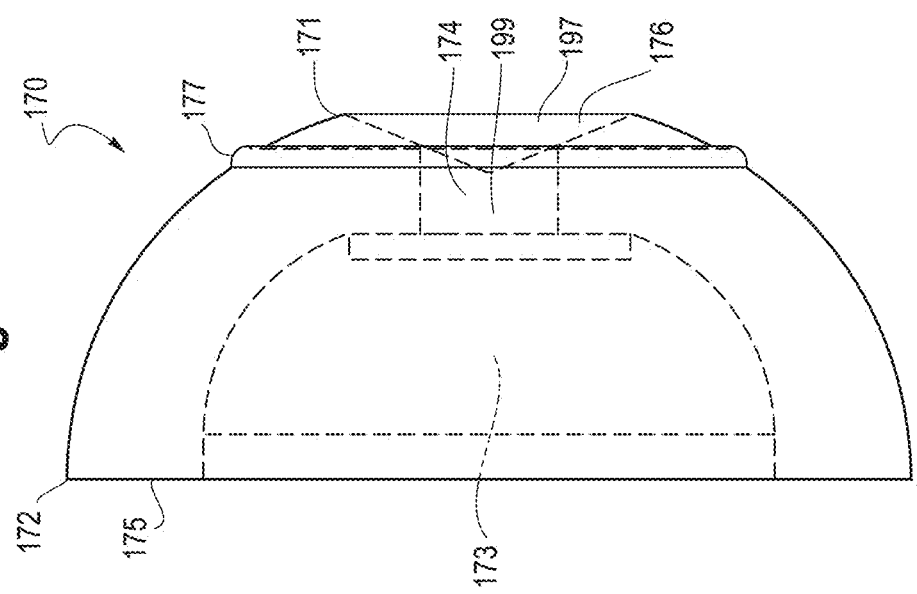

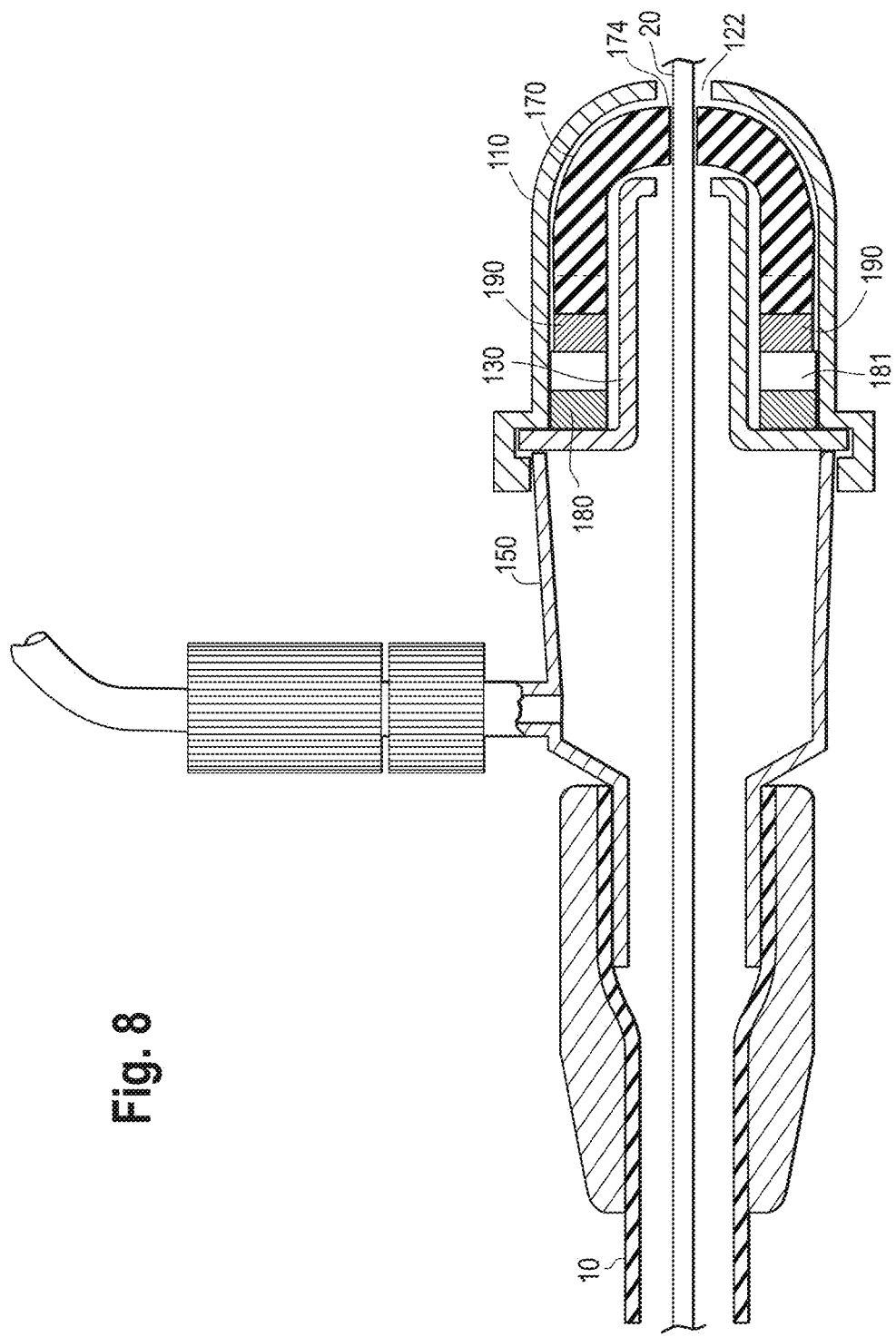

HEMOSTATIC VALVE SYSTEM

CROSS REFERENCE TO RELATED APPLICATIONS

This application claims the benefit of U.S. Provisional Application No. 62/095,272 filed on Dec. 22, 2014, the entire contents of which are hereby incorporated by reference.

TECHNICAL FIELD

This disclosure relates to medical devices. More particularly, it relates to hemostatic valve systems.

BACKGROUND

Numerous procedures have been developed that involve the percutaneous insertion of a medical device into a body vessel of a patient's body. Such a device may be introduced into the vessel by a variety of known techniques. For example, a wire guide may be introduced into a vessel using the Seldinger technique. This technique involves creating a minimally invasive opening in a vessel with a needle and inserting a wire guide into the vessel through a bore of the needle. The needle is withdrawn, leaving the wire guide in place. An introducer device is then inserted over the wire guide and into the vessel. The introducer device may be used in a conventional manner to insert into the body vessel a variety of medical devices such as catheters, guiding catheters, balloons, stents, stent grafts, and the like.

For example, an introducer device may be used to deliver and deploy an endoluminal prosthesis, such as a stent or stent graft, to treat a damaged or diseased body lumen such as a stenosis in a blood vessel. The introducer device may include a prosthesis that is radially compressed onto a delivery catheter and is covered by an outer sheath. To deploy the prosthesis, the operator withdraws the outer sheath distally over the delivery catheter, thereby exposing the prosthesis for outward expansion thereof.

One of the challenges associated with endoluminal procedures is controlling the flow of bodily fluids within the introducer device during the procedure. One or more mechanisms, such as valves may be provided when it is necessary or desired to control the flow of bodily fluids within the introducer device. For example, the introducer device may include a hemostatic valve to limit or prevent blood loss through the introducer device during a procedure.

Often, a single introducer device may be used to insert and/or deploy multiple medical devices during a procedure. For example, a single introducer device with a hemostatic valve may be used for introducing a delivery catheter for deployment of an endoluminal prosthesis within a vessel. Once the prosthesis is placed within the vessel, the introducer device with the hemostatic valve may also be used to deliver an interventional device or catheter, such as a balloon catheter, to the vessel to facilitate expansion of the deployed prosthesis. In this example, the hemostatic valve is able to provide a hemostatic seal under several conditions: (1) to seal against the delivery catheter carrying the endoluminal prosthesis when the delivery catheter is inserted into the introducer and through the valve; (2) to seal against the interventional catheter when the interventional catheter is inserted in the introducer and through the valve, and (3) to re-seal when the delivery catheter and/or the interventional catheter are removed from the introducer and valve.

SUMMARY

The present embodiments provide a hemostatic valve. In one example, the hemostatic valve assembly comprises a housing comprising a proximal end, a distal end, and a sidewall defining a housing chamber between the proximal and distal ends. At least a portion of the housing sidewall tapers radially inwardly in a proximal to distal direction. A valve member is disposed at least partially within the housing chamber, the valve member comprising an open proximal end and a distal end having an orifice formed therein and a sidewall extending between the proximal and distal ends of the valve member to form a valve cavity. The valve member is deformable between a closed configuration in which the orifice is substantially closed and an open configuration in which the orifice is open. A biasing member is disposed proximal to the valve member and is moveable between a longitudinally compressed condition and a longitudinally expanded condition. When the biasing member is in the expanded condition, it pushes the valve member longitudinally and against the tapered sidewall of the housing. The tapered sidewall of the housing thereby urges at least the distal end of the valve member radially inwardly, thus urging the orifice to the substantially closed configuration.

BRIEF DESCRIPTIONS OF THE DRAWINGS

FIG. 2 shows an exploded view of the hemostatic valve system of FIG. 1.

FIG. 3 shows a longitudinal cross sectional view of the hemostatic valve system of FIG. 1 with a side port.

FIG. 4 shows a longitudinal cross sectional view of a support member of the hemostatic valve system of FIG. 1.

FIG. 5 shows a perspective view of a valve member of the hemostatic valve system of FIG. 1.

FIG. 6 shows a side elevation view of the valve member of the hemostatic valve system of FIG. 1.

FIG. 7 shows a longitudinal cross sectional view of the valve member of the hemostatic valve system of FIG. 1.

FIG. 8 shows a longitudinal cross sectional view of the hemostatic valve system of FIG. 1 with one example of an interventional device disposed therethrough.

DETAILED DESCRIPTION

The present disclosure relates to a hemostatic valve system. In the present disclosure, the term "proximal" refers to a direction that is away from a physician during a medical procedure, while the term "distal" refers to a direction that is closest to the physician during the procedure. In addition, like reference numbers throughout the various drawings designate similar structure.

Figure 1:
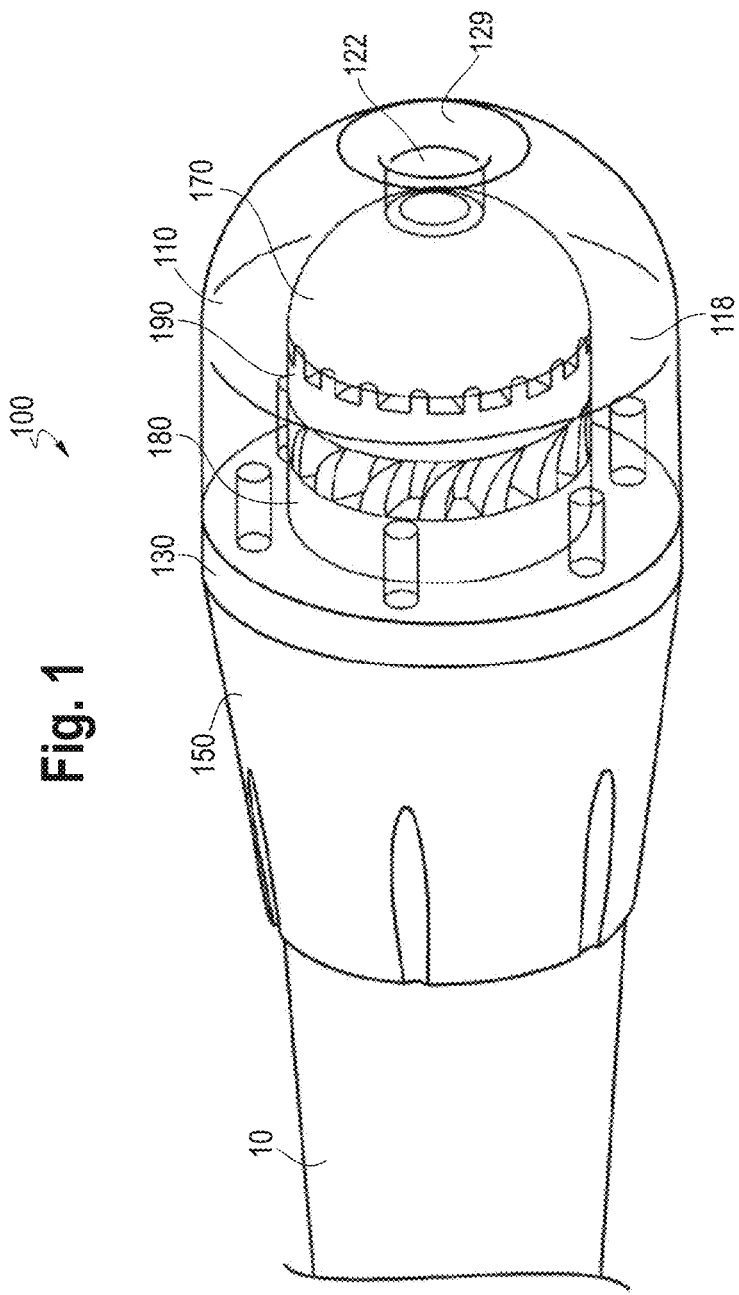
FIG. 1 shows one example of a hemostatic valve system attached to a sheath.

FIG. 1 shows one example of a hemostatic valve system 100 attached to a sheath 10. Sheath 10 may be positioned within a body vessel to provide access to the body vessel for a medical procedure. The hemostatic valve system 100 may aid in sealing a distal end of the sheath 10 to prevent a body fluid from exiting the body vessel via the sheath during the medical procedure. The hemostatic valve system 100 may enable access to the sheath 10 for delivery of an interventional device into the body vessel as further described below.

The hemostatic valve system 100 may include a tubular body 150, a supporting member 130, a biasing member 180, an engaging member 190, a valve member 170, and a housing 110.

Tubular body 150 may extend from the distal end of sheath 10. Support member 130 may be attached at the distal end of tubular body 150. Biasing member 180 may be attached at the distal end of support member 130. Engaging member 190 may be attached at the distal end of biasing member 180. Valve member 170 may be attached at the distal end of engaging member 190. Housing 110 is positioned at a distal end of hemostatic valve system 100. As described more fully below, the housing 110 may include an aperture 122. Biasing member 180, engaging member 190, and valve member 170 are at least partially received within a chamber 118 of the housing 110.

FIG. 2 shows an exploded view of the hemostatic valve system of FIG. 1. As shown in FIG. 2, tubular body 150 may include a distal portion 162 and a proximal portion 164. The outer surface of the proximal portion 164 may include engaging members 166 (e.g., ribs, threads, splines, projections or the like). The engaging members 166 may be configured to engage the distal end of the sheath (not shown) to aid in maintaining the connection between the hemostatic valve system 100 and the sheath 10 (not shown). Tubular body 150 may be engaged with support member 130.

As shown in FIG. 2, support member 130 may be configured as a tubular member having a distal end 132, a proximal end 134, a sidewall 136, and a lumen 138 extending longitudinally within the sidewall. The distal end 132 may include a distal end opening. The proximal end 134 may include a proximal end opening (not shown). In this manner, lumen 138 may include a substantially continuous pathway through the support member 130 from the distal end 132 to the proximal end 134.

The support member 130 may have a support flange 140. A support flange 140 may be positioned at the proximal end 134 of the support member 130. The support flange 140 may be formed integrally with the sidewall 136 of the support member 130 or formed separately and coupled to the sidewall 136 of the support member. The support flange 140 may extend radially outward away from the sidewall 136. The support flange 140 may at least partially encircle the sidewall 136 of the support member 130. For example, the support flange 140 may be substantially disc-shaped as shown in FIG. 2. An opening (not shown) may extend through the support flange 140. The sidewall 136 may extend distally from the support flange 140 such that the lumen 138 is in communication with the opening in the support flange. The support flange 140 may include a support surface 142, which may face in a distal direction. The opening (not shown) in the support flange 140 may be positioned approximately at the center of the support surface 142. The biasing member 180 may be in contact with the support surface 142 as further described below.

The sidewall 136 of the support member 130 may be disposed about the longitudinal axis of the hemostatic valve system 100. At least a portion of the sidewall 136 may be tapered such that an outer diameter of the support member 130 increases in a distal to proximal longitudinal direction along the portion thereof. For example, the sidewall 136 may include a tapered portion 144, which may be positioned at the distal end 132 as shown in FIG. 2. The outer diameter of the support member 130 may increase in the distal to proximal longitudinal direction along the tapered portion 144. In this manner, the distal end 132 may be configured as a beveled end 129 of the support member 130. The tapered portion 144 of the support member 130 may be configured as a straight taper or a curved taper.

The sidewall 136 of the support member may include a shaft portion 146 extending longitudinally between the tapered portion 144 and the support flange 140. The outer diameter of the support member 130 may be substantially constant along the shaft portion 146. In this manner, the outer surface of the shaft portion 146 may have a substantially cylindrical shape. The inner diameter of the support member 130 may be substantially constant between the distal end 132 and the proximal end 134. Alternatively, the inner diameter of the support member may vary longitudinally along the length thereof.

As shown in FIG. 2, biasing member 180 may be configured as a tubular member having a distal end 181, a proximal end 182, and a lumen 183 extending longitudinally within the biasing member.

The biasing member 180 may have any suitable configuration capable of longitudinal compression. For example, the biasing member may be configured as a coiled spring, flat wire spring, or in another example, the biasing member 180 may be configured as a feather spring as shown in FIG. 2. More specifically, the biasing member 180 having a feather spring configuration may include a base portion 184 and one or more spring members 185 extending distally from the base portion. The base portion 184 may be configured as an annular member (e.g., an annular ring) at least partially encircling the longitudinal axis of the hemostatic valve system 100. The spring members 185 may be configured as substantially flat blade-shaped or vane-shaped members extending distally from the base portion 184 as shown in FIG. 2. Each spring member 185 may be angled relative to the distal surface of the base portion 184. For example, each spring member 185 may form an acute angle with the distal surface of the base portion 184 such that each spring member 185 extends distally and circumferentially relative to the longitudinal axis of the valve system 100. Additionally, or alternatively, each spring member 185 may be angled or turned in a fan blade like configuration relative to the base portion 184.

The biasing member 180 may include any suitable number of spring members 185. The number of spring members 185 may be selected to provide the desired expansion force. The spring members 185 may be spaced circumferentially about the base portion 184. For example, the spring members 185 may be distributed about the base portion 184 to provide a substantially balanced force against the valve member 170 circumferentially about the rim at the proximal end 172 thereof.

As shown in FIG. 2, engaging member 190 may be configured as a tubular member having a distal end 191, a proximal end 192, and a lumen 193 extending longitudinally within the engaging member 190. The engaging ember 190 may include a base portion 194 and one or more extensions 195 extending distally from the base portion 194. The base portion 194 may be configured as an annular member (e.g., an annular ring) at least partially encircling the longitudinal axis of the hemostatic valve system 100. The extensions 195 may extend distally from the distal end of the base portion 194 as shown in FIG. 2. The extensions 195 may be distributed circumferentially about the base portion 194 and spaced from one another. In this manner, a recess 196 may be formed between each pair of adjacent extensions 195. The extensions 195 and recesses 196 may collectively form a serrated distal end 191 of the engaging member 190. The serrated distal end 191 may aid in engaging the valve member 170 as further described below.

As shown in FIG. 2, valve member 170 may be configured as a dome or bowl-shaped member having a distal end 171 and a proximal end 172. As shown, the valve member has a hemispherical configuration. A cavity 173 may be formed within the valve member 170 between the distal end 171 and the proximal end 172.

As shown in FIG. 2, housing 110 may include a distal end 112 and a proximal end 114. An outer wall 116 of the housing 110 may surround a chamber 118 disposed within the outer wall. The outer wall 116 may be disposed about a longitudinal axis of the hemostatic valve system 100, which axis may be coextensive with a longitudinal axis of the sheath 10 (shown in FIGS. 8 and 9).

At least a portion of the outer wall 116 may be tapered such that an inner diameter of the housing 110 increases in a distal to proximal longitudinal direction along the portion thereof. The taper may be configured as a straight taper, such that an inner surface of the outer wall 116 may have a substantially frustoconical shape along the tapered portion. Alternatively, the taper may be configured as a rounded taper as shown in FIG. 2. In other words, the inner surface of the outer wall 116 may have a curved or dome shape along the tapered portion. In this manner, the outer wall 116 of the housing 110 may be configured as a dome substantially surrounding the chamber 118 formed by the outer wall. For example, the inner surface of the outer wall 116 may have a shape similar to a spherical dome (e.g., a hemisphere) or a spheroidal dome along the tapered portion. An outer surface of the outer wall 116 may have a shape similar to the inner surface as shown in FIG. 2. For example, the outer surface of the distal portion 120 of the outer wall 116 may be dome-shaped. Alternatively, the thickness of the outer wall may vary longitudinally such that the outer surface of the outer wall 116 has a different shape than the inner surface. For example, an outer diameter of the outer wall may be substantially constant along the tapered portion of the outer wall. In this manner, the outer surface of the outer wall may be substantially cylindrical.

A cross sectional area of the chamber 118 may be defined by the inner surface of the outer wall 116. At least a portion of the chamber 118 may be tapered such that the chamber has an increasingly larger cross sectional area in the distal to proximal longitudinal direction, as shown in FIG. 2. The distal portion of the chamber 118 may be disposed within the distal portion 120 of the outer wall 116. The taper of the chamber 118 may be configured as a straight taper or a rounded taper as described above with reference to the taper of the outer wall 116.

The housing 110 may include an aperture 122 formed in the outer wall 116. The aperture 122 may be positioned at the distal end 112 of the housing 110 and disposed about the longitudinal axis of the hemostatic valve system 100. For example, the aperture 122 may be positioned at or aligned with an apex of the domed housing 110 as shown in FIG. 2. The aperture 122 may have any suitable cross sectional shape including, for example, circular, elliptical, rectangular, or triangular. The aperture 122 may include a beveled entrance 129 at the distal end thereof as shown in FIG. 1 and FIG. 5. This may aid in guiding an interventional device into the aperture for advancement through the hemostatic valve system 100 as further described below.

The outer wall 116 of housing 110 may include a proximal portion 124 extending distally from the distal portion 120 as shown in FIGS. 1-3. The housing 110 may have a substantially constant inner diameter and/or outer diameter along the proximal portion 124. For example, the inner surface and the outer surface of the proximal portion 124 may be substantially cylindrical about the longitudinal axis of the hemostatic valve system 100 as shown in FIGS. 1-3.

The proximal end 114 of the housing 110 may be configured as an open end. In this manner, the chamber 118 may include a continuous pathway through the housing 110 from the aperture 122 at the distal end 112 to the open proximal end 114. A medical device such as an interventional device (not shown) may be advanced into the housing 110 through the aperture 122, distally through the chamber 118, and out of the housing 110 through the open proximal end 114 to introduce the medical device (not shown) into the sheath 10 as further described below.

FIG. 3 shows a longitudinal cross sectional view of the hemostatic valve system 100 of FIG. 1 with a side port 160. The tubular body 150 may be engaged with the support member 130 as shown in FIG. 3. The tubular body 150 may include a distal end 152, a proximal end 154, a sidewall 156, and a lumen 158 extending longitudinally within the sidewall. The tubular body 150 may be disposed about the longitudinal axis of the hemostatic valve system 100. The distal end 152 may include a distal end opening. The proximal end 154 may include a proximal end opening. In this manner, the lumen 158 may include a substantially continuous pathway through the tubular body 150 from the distal end 152 to the proximal end 154.

As shown in FIG. 3, the tubular body 150 may include a side port 160, which may extend outward from the sidewall 156. The side port 160 may be in fluid communication with the lumen 158. The side port 160 may include a coupling (e.g., a Luer lock coupling), which may enable attachment of a syringe, tubing, or other apparatus to the side port. The side port 160 may enable introduction of a fluid (e.g., medication, contrast medium, saline, or other suitable fluid) into the lumen 158 of the tubular body 150 and distally into the sheath 10.

As shown in FIG. 3, the distal end 152 of the tubular body 150 may be engaged with the support member 130. For example, the distal end 152 of the tubular body 150 may be coupled to the flange 140 of the support member 130 as shown in FIGS. 1 and 3. The tubular body 150 may be coupled to the support member 130 using any suitable type of connection including, for example, an adhesive connection, a snap fit connection, a threaded connection, or a fastener (e.g., a screw, a bolt, or a rivet). In one example, the tubular body 150 may be formed integrally with the support member 130. In one example, a secondary sealing member (e.g., a conventional valve o-ring or disc (not shown) may be disposed between the tubular body 150 and the support member 130 The secondary sealing member may supplement the valve member 170 in sealing the distal end of the sheath. In one example, the support member 130 is at least partially received within the lumen 158 of the tubular body 150 as further described below with reference to FIG. 10.

The sidewall 156 of the tubular body 150 may include a distal portion 162 and a proximal portion 164. The distal portion 162 may have a larger outer diameter than the proximal portion 164 as further described below. The outer diameter and/or the inner diameter of the sidewall 156 may be substantially constant along the distal portion 162 of the tubular body 150. In this manner, the outer surface and/or the inner surface of the distal portion 162 of the tubular body 150 may be substantially cylindrical about the longitudinal axis. Alternatively, the outer diameter and/or the inner diameter may taper along the distal portion of the tubular body 150. For example, the outer diameter and the inner diameter may decrease in the distal to proximal longitudinal direction along the distal portion 162 of the tubular body 150 as shown in FIGS. 1-3. In this manner, the outer surface and the inner surface of the distal portion 162 may have a frustoconical shape about the longitudinal axis.

The sidewall 156 of the tubular body 150 may taper from the larger diameter of the distal portion 162 to the smaller diameter of the proximal portion 164. The proximal portion 164 may be configured to be received in the distal end of the sheath 10 to couple the hemostatic valve system 100 to the sheath 10. As shown in FIG. 2, the outer surface of the proximal portion 164 may include engaging members 166 (e.g., ribs). The engaging members 166 may be configured to engage the distal end of the sheath 10 to aid in maintaining the connection between the hemostatic valve system 100 and the sheath 10. The sheath 10 may include a flared distal end configured to fit over the proximal portion 164 of the tubular body 150 as shown in FIG. 3.

As shown in FIG. 3, the support member 130 may be disposed at least partially within the chamber 118 of the housing 110. A space may be defined between the inner surface of the outer wall 116 of the housing 110 and the outer surface of the sidewall 136 of the support member 130. The valve member 170, the biasing member 180, and/or the engaging member 190 may be received within the space as further described below. The valve member 170, the biasing member 180, and/or the engaging member 190 may be capable of moving longitudinally within the space relative to the housing 110 and the support member 130.

The outer surface of the sidewall 136 of the support member 130 may be shaped to correspond to the inner surface of the outer wall 116 of the housing 110. In other words, the outer surface of the sidewall 136 of the support member 130 may have a shape similar to the inner surface of the outer wall 116 of the housing 110. For example, the shape of the inner surface of the outer wall 116 of the housing 110 along the distal portion 120 thereof and the shape of the outer surface of the sidewall 136 of the support member 130 along the tapered portion 144 thereof may substantially correspond to one another. Additionally, or alternatively, the shape of the inner surface of the outer wall 116 of the housing 110 along the proximal portion 124 thereof and the shape of the outer surface of the sidewall 136 of the support member 130 along the shaft portion 146 thereof may substantially correspond to one another. In this manner, a distance between the inner surface of the outer wall 116 of the housing 110 and the outer surface of the sidewall 136 of the support member 130 may be substantially constant along at least a portion of the lengths thereof. For example, the distance between the inner surface of the outer wall 116 of the housing 110 and the outer surface of the sidewall 136 of the support member 130 may be substantially constant along the length of the tapered portion 144 of the sidewall 136 and/or along the length of the shaft portion 146 of the sidewall 136. Such uniform spacing may aid in supporting the valve member 170 between the inner surface of the outer wall 116 of the housing 110 and the outer surface of the sidewall 136 of the support member 130 as further described below.

As seen in FIG. 3, the housing 110 may be coupled to the support member 130. For example, an engaging portion 126 of the housing 110 may include a Groove in an inner surface thereof. The groove may extend circumferentially about the inner surface of the engaging portion 126. An outer edge of the flange 140 of the support member 130 may be received in the groove of the housing 110. The housing 110 may be pressed onto the support member 130 until the flange 140 snaps into the groove. In this manner, the housing 110 may be coupled to the support member 130 using a snap fit connection and/or using any other suitable type of connection. For example, the engaging portion 126 of the housing 110 may include internal threads configured to engage with external threads on the outer edge of the flange 140 of the support member 130. In other examples, the engaging portion 126 of the housing 110 may be coupled to the support member 130 using an adhesive or a fastener (e.g., a screw, a bolt, or a rivet).

The support member 130 may be at least partially disposed within the cavity 173 of the valve member 170. For example, the tapered portion 144 of the support member 130 may be disposed within the cavity 173 as shown in FIG. 3.

The valve member 170 may be disposed within the chamber 118 of the housing 110 in the space between the housing 110 and the support member 130 as shown in FIG. 3. The valve member 170 may be disposed at least partially within the distal portion of the chamber 118. In this manner, at least a portion of the valve member 170 may be disposed between the distal portion 120 of the housing 110 and the tapered portion 144 of the support member 130. This may aid in biasing the valve member 170 toward a closed configuration and/or providing support to the valve member as further described below.

The wall of the valve member 170 may have a thickness corresponding to the width of the space between the housing 110 and the support member 130. The valve member 170 may substantially fill the space along at least a portion of the length of the space. The outer surface and the inner surface of the bowl-shaped valve member 170 may be tapered. For example, the outer surface of the valve member 170 may have a shape similar to the shape of the inner surface of the distal portion 120 of the housing 110. Additionally, or alternatively, the inner surface of the valve member 170 may have a shape similar to the shape of the outer surface of the tapered portion 144 of the support member 130. In one example, the inner surface and the outer surface of the valve member 170 may have a shape similar to a spherical dome (e.g., a hemisphere) or a spheroidal dome. The outer surface of the valve member 170 may be engaged by the inner surface of the housing 110. The inner surface of the valve member 170 may be engaged by the support member 130.

The valve member 170 may include an orifice 174 at the distal end 171. The proximal end 172 of the valve member 170 may be configured as an open end. In this manner, the cavity 173 may include a substantially continuous pathway through the valve member 170 from the distal end 171 to the proximal end 172.

FIG. 4 shows a longitudinal cross sectional view of a support member 130. The support member 130 may include an engaging rim 141 positioned at the distal end 132. The engaging rim 141 may be configured to engage the valve member 170 to aid in urging the valve member toward a closed configuration as further described below. The engaging rim 141 may include a notch 143 in an inner surface of the support member 130 at the distal end 132. The notch 143 may extend circumferentially around the sidewall 136 of the support member 130. An outer ridge 145 and an inner ridge 147 may be positioned on opposing sides of the notch 143. The notch 143 may include angled walls. In this manner, the notch 143 may be configured as a substantially V-shaped trough positioned between the outer ridge 145 and the inner ridge 147.

In response to movement of the valve member 170 toward an open configuration as further described below, the material of the valve member may be urged against and/or flow into the notch 143 between the outer ridge 145 and the inner ridge 147. This may cause deformation of the surface of the valve member 170 in contact with the engaging rim 141. Such deformation may urge the valve member 170 toward the closed configuration. For example, the angled walls of the notch 143 may aid in urging the material of the valve member 170 out of the notch. In other words, the shape of the engaging rim 141 may cause the material of the valve member 170 to be urged out of the notch 143, which may cause the valve member 170 to be urged toward the closed configuration.

FIGS. 5-7 show a perspective view, a side elevation view, and a longitudinal cross sectional view, respectively, of the valve member 170. The valve member 170 may include a dimple 176 positioned at the distal end 171. The dimple 176 may be configured as a depression in the outer surface of the valve member 170. The orifice 174 of the valve member 170 may be positioned within the dimple 176 (e.g., approximately at the center of the dimple). The dimple 176 may aid in guiding an interventional device (not shown) toward the orifice 174 to advance the interventional device through the valve system as further described below.

As shown in FIGS. 5-7, a ridge 177 may be formed in the outer surface of the valve member 170. The ridge 177 may be positioned near the distal end 171 of the valve member. The ridge 177 may be configured as a raised portion of the outer surface of the valve member 170. The ridge 177 may extend circumferentially around the valve member 170. For example, the ridge 177 may circumscribe substantially the entire outer surface of the valve member 170 as shown in FIG. 5. In this manner, the ridge 177 may be substantially ring-shaped. In use, the ridge 177 may engage the inner surface of the housing 110. In this manner, the ridge 177 may aid in forming a seal between the valve member 170 and the housing 110.

As shown in FIG. 7, the inner surface of the valve member 170 may include a flattened portion 178 positioned near the distal end 171. The flattened portion 178 may be configured as a substantially planar surface positioned at a distal end of the chamber 118. A channel 179 may be formed in the inner surface of the valve member 170. The channel 179 may extend circumferentially along the inner surface of the valve member 170. For example, the channel 179 may extend circumferentially around substantially the entire inner surface of the valve member 170, in this manner, the channel 179 may be substantially ring-shaped. The channel 179 may at least partially circumscribe the flattened portion 178 of the valve member 170. For example, the flattened portion 178 may be positioned within an open center of the ring-shaped channel 179. The channel 179 aids in enabling the valve member 170 to flex (e.g., upon moving between the closed configuration and the open configuration). For example, the thickness of the valve member 170 at the channel 179 may be reduced relative to the remainder of the valve member 170. The portion of the valve member 170 with the reduced thickness may act as a flexible hinge to enhance the flexibility of the valve member 170.

The orifice 174 may include an opening extending partially or entirely through the valve member 170. The orifice 174 may provide a pathway through the valve member 170 from the exterior of the valve member into the cavity 173. In one example, the orifice 174 includes a hole (not shown) through the valve member 170, in another example, the orifice 174 includes a slit 199 formed in the valve member 170. The slit 199 may extend partially or entirely through the valve member 170 to form the orifice 174. For example, the slit 199 may extend entirely through the valve member 170 as shown in FIG. 5. In one example (not shown), the orifice 174 may include a first slit formed in the outer surface of the valve member 170 and a second slit formed in the inner surface of the valve member opposite the first slit. The first slit and the second slit may be angled relative to one another. For example, the first slit and the second slit may be oriented perpendicular to one another. In other examples, the first slit and the second slit may be oriented at any other angle relative to one another. Each of the first slit and the second slit may extend partially (e.g., approximately half way) through the valve member 170. In this manner, the first slit and the second slit may intersect one another to form the orifice 174 extending through the valve member 170.

The orifice 174 may be positioned approximately at the apex 197 of the bowl-shaped valve member 170 and aligned with the dimple 176 of the valve member 170 at a point along the longitudinal axis of the valve system 100. The orifice 174 may be substantially aligned with the aperture 122 of the housing 110 and the distal end opening of the support member 130. In this manner, an interventional device may be advanced through the aperture 122 and the orifice 174 and into the support member 130 as further described below.

The valve member 170 may be deformable between a closed configuration (see FIG. 3) and an open configuration (see FIG. 8). FIG. 3 shows the hemostatic valve system 100 with the valve member 170 in the closed configuration. In the closed configuration, the orifice 174 may be substantially closed or sealed. To that end, one or more edges 189 of the valve member 170 adjacent to the orifice 174 may be in abutting contact with one another. For example, edges 189 of the valve member 170 opposite the slit that defines the orifice 174 may be in abutting contact with one another. Body fluid may be substantially prevented from flowing through the orifice 174 in the closed configuration. In this manner, the distal end 11 of the sheath 10 may be substantially sealed by the hemostatic valve system 100 with the valve member 170 in the closed configuration, and as a result, any fluid flowing distally through the sheath 10 is prevented from flowing through the valve system 100 with the valve member 170 in the closed configuration.

FIG. 8 shows a longitudinal cross sectional view of the hemostatic valve system 100 of FIG. 1 in the open configuration with one example of an interventional device 20 disposed therethrough. The interventional device 20 may include any device, object, or structure that supports, repairs, or replaces, or that may be used alone or in combination with other devices, objects, or structures, to support, repair, or replace a body part or a function of that body part. Examples of interventional devices include sheaths, catheters, wire guides, cardiac leads, vessel occlusion devices, filters, stents, stent grafts, and delivery and deployment devices.

A proximal end of the interventional device 20 may be introduced through the aperture 122 in the housing 110 and brought into contact with the valve member 170. The interventional device 20 may be advanced proximally through the orifice 174 of the valve member 170. This may cause the edges 189 of the valve member 170 adjacent to the orifice 174 to be pushed outward to accommodate the interventional device 20. The valve member 170 may begin to deform as the orifice 174 is pushed open. To that end, the valve member 170 may be formed from a substantially compliant material such that as the orifice 174 is pushed open, the material of the valve member 170 is capable of flowing into the recesses 196 of the engaging member. In this manner, as the valve member 170 deforms, the material at the proximal end 172 of the valve member 170 may flow into the recesses 196 of the engaging member 190 such that the proximal rim 175 of the valve member takes on a shape corresponding to the serrated distal end 191 of the engaging member. This may increase the contact area between the engaging member 190 and the valve member 170, which may aid in supporting the valve member.

The material of the valve member 170 may be sufficiently elastic so that the valve member is biased toward its initial, non-deformed closed configuration as illustrated in FIG. 1. Additionally, the distal force exerted by the biasing member 180 may urge the valve member 170 distally within the housing 110 as described above, which may cause the valve member to squeeze the interventional device 20 to form a seal around the outer surface of the interventional device 20. The recesses 196 of the engaging member 190 may receive a sufficient amount of the material of the valve member 170 that further compression of the biasing member 180 is unnecessary to accommodate the interventional device 20. The interventional device 20 may have a sufficiently small outer diameter, that the volume of material of the valve member 170 that is displaced upon passage of the interventional device through the orifice 174 is able to fit within the available volume provided by the recesses 196 of the engaging member 190. In this manner, the engaging member 190 may remain substantially stationary relative to the support member 130 and the housing 110.

The interventional device 20 may be advanced further proximally through the support member 130 and the tubular body 150 of the hemostatic valve system 100 and into the sheath 10. The interventional device 20 may be advanced further proximally through the sheath 10 to a target location within the patient's body. The interventional device 20 may be retracted distally and removed from the hemostatic valve system 100. The material of the valve member 170 may be sufficiently elastic and compliant that, upon removal of the interventional device 20, the valve member may return to the closed configuration shown in FIG. 3. The force applied by the biasing member 180 and the shapes of the valve member 170, the housing 110, and/or the engaging member 190 may aid in biasing the valve member 170 toward the closed configuration as described above. In this manner, the hemostatic valve system 100 may be configured as a dynamic sealing system that actively closes to seal around the interventional device 20 and also seal upon removal of the interventional device 20 therefrom.

Figure 9:
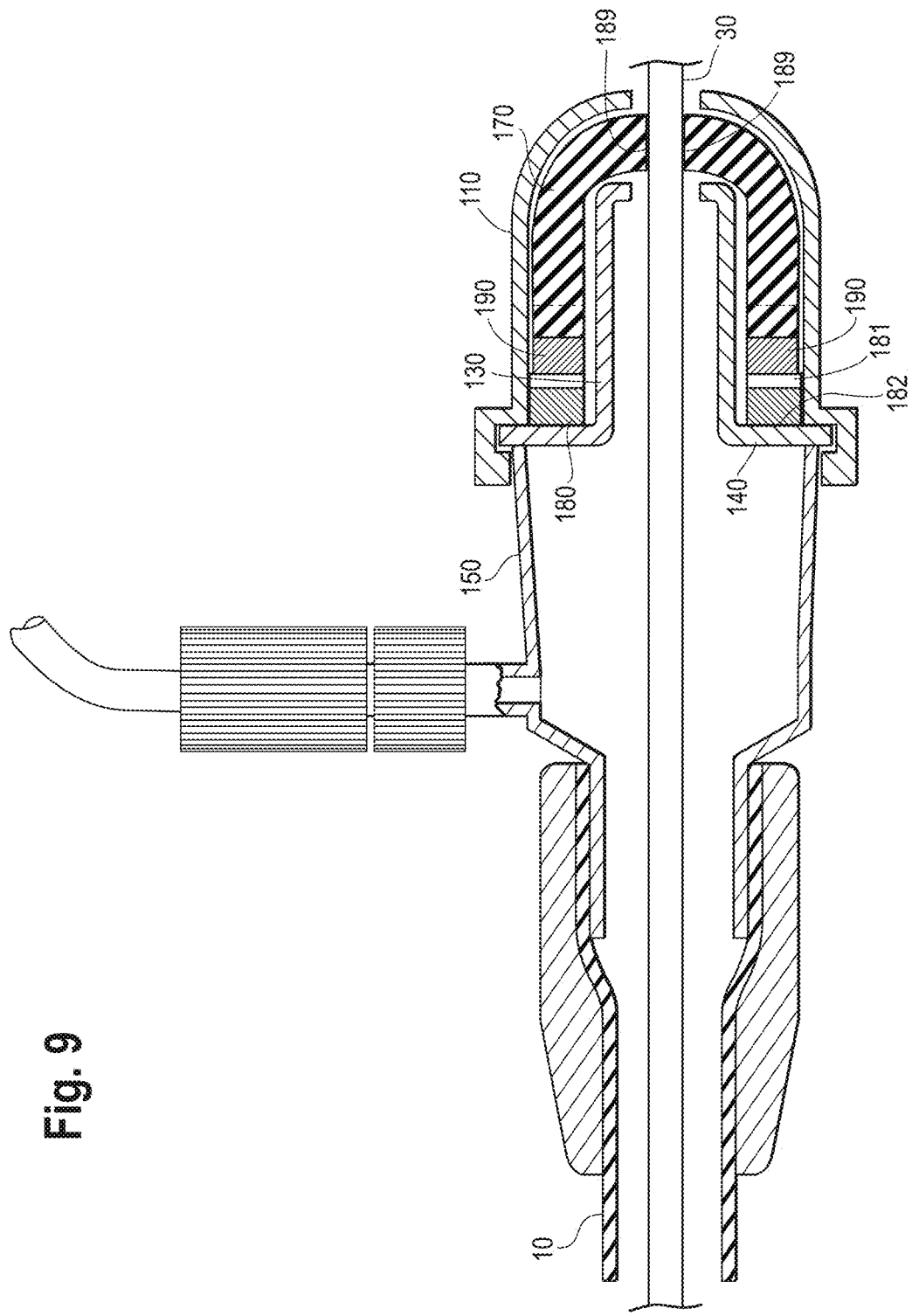
FIG. 9 shows a longitudinal cross sectional view of the hemostatic valve system of FIG. 1 with another example of an interventional device disposed therethrough.

FIG. 9 shows a longitudinal cross sectional view of the hemostatic valve system of FIG. 1 with another example of an interventional device 30 disposed therethrough. The interventional device 30 may be any suitable interventional device as described above with reference to the interventional device 20. The interventional device 30 may have a larger outer diameter than the interventional device 20.

A proximal end of the interventional device 30 may be introduced through the aperture 122 in the housing 110 and through the orifice 174 of the valve member 170. This may cause deformation of the valve member 170 as described above with reference to FIG. 8. As the valve member 170 deforms, the material of the valve member may flow into the recesses 196 of the engaging member 190 such that the proximal rim 175 of the valve member takes on a shape corresponding to the serrated distal end 191 of the engaging member. The interventional device 30 may have a sufficiently large outer diameter that the orifice 174 may be further expanded after filling the recesses 196 of the engaging member 190 with the material of the valve member 170 as described above. This may cause the material of the valve member to be pushed proximally in the space between the outer wall 116 of the housing 110 and the sidewall 136 of the support member 130 as shown in FIG. 9. This may cause the engaging member 190 to move proximally relative to the support member 130 and the housing 110, which may cause further compression of the biasing member 180 to accommodate the interventional device 30.

The interventional device 30 may be advanced further proximally through the support member 130 and the tubular body 150 of the hemostatic valve system 100 and into the sheath 10. The interventional device 30 may be advanced further proximally through the sheath 10 to a target location within the patient's body. The interventional device 30 may be retracted distally and removed from the hemostatic valve system 100. The material of the valve member 170 may be sufficiently elastic and compliant that, upon removal of the interventional device 30, the valve member may return to the closed configuration. The engaging member 190 may move distally relative to the support member 130 and the housing 110 to return to its initial position within the housing 110, and the biasing member 180 may expand longitudinally. The force applied by the biasing member 180 and the shapes of the valve member 170, the housing 110, and/or the engaging member 190 may aid in biasing the valve member toward the closed configuration as described above.

FIGS. 8-9 illustrate the hemostatic valve system 100 with the valve member 170 in the open configuration. One or more edges 189 of the valve member 170 adjacent to the orifice 174 may be spaced from one another such that they are not in abutting contact. For example, edges 189 of the valve member 170 opposite the slit 199 that defines the orifice 174 may be spaced from one another and thus the orifice 174 is open. In this manner, an interventional device may be capable of passing through the valve member 170 to introduce the interventional device through the hemostatic valve system 100 and into the sheath 10 as shown in FIGS. 8-9. The edges 189 of the valve member 170 adjacent to the orifice 174 may be in contact with an interventional device to provide a seal around the interventional device. In this manner, body fluid may be substantially prevented from flowing through the orifice 174 and around the interventional device, and the distal end of the sheath 10 may be substantially sealed by the hemostatic valve system 100.

The shapes of the housing 110, the support member 130, and/or the valve member 170 may aid in biasing the valve member toward the closed configuration. More specifically, the valve member 170 may be urged distally within the chamber 118 of the housing 110 by the biasing member 180 and/or the engaging member 190. As the valve member 170 is urged distally, the inner surface of the outer wall 116 of the housing 110 may engage the outer surface of the valve member 170. For example, the inner surface of the distal portion 120 of the housing 110 (e.g., the tapered inner surface) may engage the outer surface of the valve member 170 (e.g., the tapered outer surface). Urging the valve member 170 distally into the tapered distal portion 120 of the inner surface of the housing 110 may cause the distal end 171 of the valve member to be squeezed inward or radially compressed by the inner surface of the housing. This may cause the edges 189 of the valve member 170 adjacent to the orifice 174 to be urged toward one another. In this manner, the orifice 174 may be urged toward the closed configuration. The position of the support member 130 within the cavity 173 of the valve member 170 may aid in preventing the valve member 170 from collapsing inward as the valve member 170 is urged toward the closed configuration. In this manner, the support member 130 may provide support to the valve member 170 from within valve chamber 118.

The biasing member 180 may be longitudinally compressible. Upon compression of the biasing member 180, which may occur upon insertion of an interventional device into the valve system 100, for example, the proximal end 182 of the biasing member 180 may press against the support flange 140 and exert a longitudinal force in the distal direction. The distal end 181 of the biasing member 180 may be in contact with the valve member 170 and/or the engaging member 190. In this manner, the longitudinal force exerted by the biasing member 180 may urge the valve member 170 distally within the chamber 118. This may aid in biasing the valve member 170 toward the closed configuration as described above.

Upon longitudinal compression of the biasing member 180, the spring member(s) 185 may be flexed, compressed, or bent toward the distal surface of the base member 184. The angle between the biasing member(s) 185 and the distal surface of the base member 184 may be reduced upon compression of the biasing member 180. Each spring member 185 may have a contoured outer edge. For example, the outer edge of each spring member 185 may be curved such that, as the spring member 185 is flexed toward the base member 184, the outer edge of each spring member 185 remains within the outer diameter of the base member. In this manner, the outer diameter of the biasing member 180 may remain constant during longitudinal compression of the biasing member. In other words, the outer diameter of the biasing member 180 may not expand during longitudinal compression of the biasing member.

The engaging member 190 may be disposed within the chamber 118 of the housing and proximal of the valve member 170. For example, the engaging member 190 may be disposed between the valve member 170 and the biasing member 180 as shown in FIGS. 1-3. The support member 130 may be at least partially disposed within the lumen 193 of the engaging member 190, with the engaging member 190 being longitudinally moveable relative to the support member 130 and the housing 110. The proximal end 192 of the engaging member 190 may be in contact with the biasing member 180. The distal end 191 of the engaging member 190 may be in contact with the valve member 170. In this manner, the biasing member 180 may urge the engaging member 190 distally within the chamber 118 and, in turn, urge the valve member 170 distally within the chamber 118. As mentioned previously, as the valve member 170 is urged distally, the tapered inner surface of the outer wall 116 of the housing causes the valve member 170 to be urged radially inwardly into a closed or sealing configuration.

Figure 10:
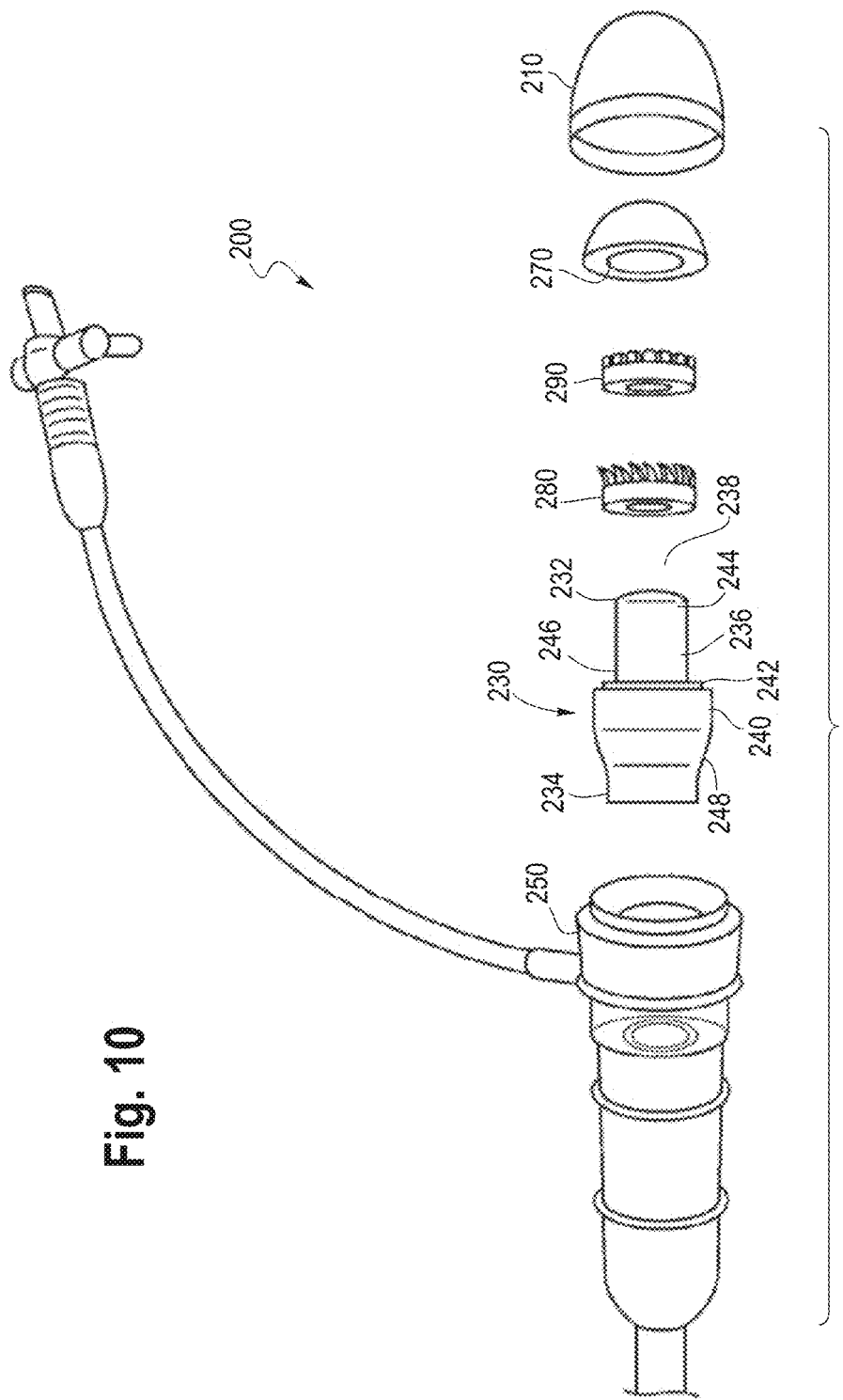
FIG. 10 shows an exploded view of another example of a hemostatic valve system.

FIG. 10 shows an exploded view of another example of a hemostatic valve system 200. The valve system 200 may be similar to the hemostatic valve system 100 described above. For example, the valve system 200 may include a housing 210, a tubular body 250, a valve member 270, a biasing member 280, and an engaging member 290, which may be configured substantially as described above with reference to the hemostatic valve system 100. The valve system 200 may include a support member 230, which may have a somewhat different configuration than the support member 130 described above. The support member 230 may be configured as a tubular member having a distal end 232 with a distal end opening, a proximal end 234 with a proximal end opening, a sidewall 236, and a lumen 238 extending longitudinally within the sidewall. A support flange 240 may be positioned at or near the proximal end 234 of the support member 230. The support flange 240 may extend radially outward away from the sidewall 236. The support flange 240 may include a support surface 242, which may face in a distal direction. The biasing member 280 may be in contact with the support surface 242 as described above with reference to the hemostatic valve system 100. The sidewall 236 may include a tapered portion 244, which may be positioned at the distal end 232. The support member 230 may include an engaging rim (not shown in detail) as described above with reference to the engaging rim 141 of the support member 130. The sidewall 236 may include a shaft portion 246 extending longitudinally between the tapered portion 244 and the support flange 240.

The support member 230 may further include a plug member 248 extending proximally from the support flange 240. The plug member 248 may be formed integrally with the support flange 240 or formed separately and then attached to the support flange. An outer surface of the plug member 248 may be tapered. For example, an outer diameter of the plug member 248 may decrease in a distal to proximal longitudinal direction. The plug member 248 may be engaged by the distal end of the tubular body 250. To that end, the outer surface of the plug member 248 may be sized and shaped to correspond to the inner surface of the distal end of the tubular body 250. In this manner, the plug member 248 may be configured to be disposed at least partially within the lumen of the tubular body 250. With the plug member 248 in place within the body 250, the side port of the body may be positioned proximal of the proximal end 234 of the support member 230. The housing 210 may be coupled to the tubular body 250 using any suitable type of connection as described above with reference to the hemostatic valve system 100. In this manner, the support member 230 may be maintained in position between the housing 210 and the body 250.

The hemostatic valve systems 100, 200 described herein may be capable of sealing around interventional devices having a wide range of sizes. The valve systems 100, 200 may be capable of sealing around relatively large interventional devices and recovering to seal around relatively small interventional devices or to return to the closed and sealed position (e.g., after removal of all interventional devices). In one non-limiting example, the hemostatic valve system 100 may be capable of sealing around a relatively large dilator (e.g., about 24 Fr) and then recovering to seal around a relatively fine guide wire (e.g., having an outer diameter of about 0.018 in) while further recovering to completely seal when all interventional devices and/or wires have been removed. The valve systems described herein may be capable of achieving a balance between being tight enough to seal with nothing extending across and through the valve and conformable enough to allow easy passage of interventional devices therethrough.

The hemostatic valve systems described herein may also be capable of sealing around one or more devices having a wide range of sizes at the same time. For example, the hemostatic valve system 100, 200 may be capable of sealing around two interventional devices at the same time.

The hemostatic valve systems 100, 200 described herein, or various components thereof, may be formed from any suitable materials. Suitable polymeric materials may include, for example, silicone, polyamide (nylon), polyurethane, polyether ether ketone (PEEK), polyester (e.g., polyethylene terephthalate (PET)), polyethylene, polyethylene oxide (PEO), polystyrene, polypropylene, or blends or copolymers thereof. The valve member may be formed from any suitable elastomeric material including, for example, silicone; urethane; rubber; polytetrafluoroethylene (PTFE); a polyamide (e.g., nylon 12); a polyamide block copolymer (e.g., PEBA); a polyolefin; a polyester (e.g., PET); a polyurethane copolymer with MDI, HMD or TDI hard segment and aliphatic polyester, polyether, or polycarbonate soft segment (e.g., Pellethane, Estane or Bionate); polyester copolymers with 4GT (PBT) hard segments and aliphatic polyester or polyether soft segments (e.g., Hytrel, Pelprene or Arnitel)); or blends or copolymers thereof. In one example, the valve member 170, 270 may be formed from a substantially compliant material such as, for example, a high consistency rubber (HCR) including silicone or LSR Silicone Rubber. The material may have a high tear strength and/or a high elongation.

While various embodiments of the invention have been described, the invention is not to be restricted except in light of the attached claims and their equivalents.

We claim:

1. A hemostatic valve assembly comprising:
   a housing comprising a proximal end, a distal end and a side wall defining a housing chamber between the proximal and distal ends, wherein at least a portion of the housing side wall tapers radially inwardly in a proximal to distal direction to form a continuously curved inner surface;
   a tubular sheath extending proximally from the housing and comprising a proximal end and a distal end and a sheath lumen extending therebetween;
   a valve member disposed at least partially within the housing chamber, the valve member comprising an open proximal end, a distal end having an orifice formed therein, a side wall extending between the proximal and distal ends of the valve member to form a valve cavity, and a continuously curved outer surface, the valve member being deformable between a closed configuration in which the orifice is substantially closed and an open configuration in which the orifice is open; and
   a biasing member disposed proximal to the valve member and moveable between a longitudinally compressed condition and a longitudinally expanded condition,
   wherein, when in the longitudinally expanded condition, the biasing member is configured to push the valve member longitudinally and against the continuously curved inner surface of the side wall of the housing,
   wherein the continuously curved inner surface of the side wall of the housing is configured to urge at least the distal end of the valve member radially inwardly, thus urging the orifice to a substantially closed configuration,
   wherein the housing comprises an open aperture at its distal end such that an interventional device may be introduced proximally through the open aperture, advanced through the orifice, advanced through the housing chamber, and into the sheath, and
   wherein the orifice of the valve member is biased in the closed configuration and wherein when the orifice of the valve member is biased in the closed configuration, the open aperture is open.

2. The hemostatic valve assembly of claim 1, further comprising a tubular support member comprising a proximal end, a distal end and a side wall extending between the proximal and distal ends of the tubular support member to define a lumen, wherein the tubular support member is disposed at least partially within the chamber of the housing.

3. The hemostatic valve assembly of claim 2 further comprising a support flange at the proximal end of the tubular support member and extending radially outwardly from the sidewall of the tubular support member.

4. The hemostatic valve assembly of claim 3, wherein the distal end of the sheath is engageable with the tubular support member, the sheath lumen being in fluid communication with the tubular support member lumen.

5. The hemostatic valve assembly of claim 4, wherein the tubular support member comprises a plug member extending proximally from the support flange, and wherein the plug member is at least partially received within the sheath lumen.

6. The hemostatic valve assembly of claim 2, wherein the distal end of the tubular support member comprises a tapered portion disposed at least partially within the cavity of the valve member.

7. The hemostatic valve assembly of claim 6, wherein the biasing member comprises an annular base portion and a plurality of spring members extending distally from the annular base portion.

8. The hemostatic valve assembly of claim 2, wherein the biasing member comprises a proximal end, a distal end and a lumen extending longitudinally between the proximal and distal ends of the biasing member, and wherein the tubular support member extends at least partially within the lumen of the biasing member.

9. The hemostatic valve assembly of claim 2, wherein the distal end of the tubular support member comprises a tapered portion having a tapered shape, wherein the tapered shape of the tapered portion of the support member substantially corresponds to a shape of the continuously curved inner surface of the side wall of the valve member.

10. The hemostatic valve assembly of claim 1, further comprising an engaging member disposed longitudinally between the valve member and the biasing member.

11. The hemostatic valve assembly of claim 10, wherein the engaging member comprises an annular base portion and a plurality of extensions extending distally from the annular base portion.

12. The hemostatic valve assembly of claim 11 wherein one or more recesses are formed between an adjacent pair of the plurality of extensions.

13. The hemostatic valve assembly of claim 12, wherein the proximal end of the valve member is engageable with the extensions of the engaging member, and when the valve member is in the open configuration, at least a portion of the proximal end of the valve member extends into the one or more recesses of the engaging member.

14. The hemostatic valve assembly of claim 1, wherein the continuously curved outer surface of the valve member sidewall substantially corresponds to the continuously curved inner surface of the housing.

15. The hemostatic valve assembly of claim 14, wherein the continuously curved inner surface of the housing comprises a dome shape, and wherein the continuously curved outer surface of the valve member comprises a dome shape corresponding to the dome shape of the distal end of the housing.

16. The hemostatic valve assembly of claim 1 wherein the biasing member is biased in the longitudinally expanded condition.

17. A hemostatic valve assembly comprising:
   a housing comprising a proximal end, a distal end and a side wall defining a housing chamber between the proximal and distal ends, wherein at least a portion of the housing side wall tapers radially inwardly in a proximal to distal direction to form a continuously curved inner surface;

a tubular sheath extending proximally from the housing and comprising a proximal end and a distal end and a sheath lumen extending there between;

a valve member disposed at least partially within the housing chamber, the valve member comprising an open proximal end, a distal end having an orifice formed therein, a side wall extending between the proximal and distal ends of the valve member to form a valve cavity, and a continuously curved outer surface, the valve member being deformable between a closed configuration in which the orifice is substantially closed and an open configuration in which the orifice is open; and a biasing member disposed proximal to the valve member and moveable between a longitudinally compressed condition and a longitudinally expanded condition, wherein, when in the longitudinally expanded condition, the biasing member is configured to push the valve member longitudinally and against the continuously curved inner surface of the side wall of the housing, wherein the continuously curved inner surface of the side wall of the housing is configured to urge at least the distal end of the valve member radially inwardly, thus urging the orifice to a substantially closed configuration, wherein the housing comprises an open aperture at its distal end such that an interventional device may be introduced proximally through the open aperture, advanced through the orifice, advanced through the housing chamber, and into the sheath, wherein the orifice formed in the distal end of the valve member is at least partially aligned with the open aperture, and wherein the open aperture formed in the distal end of the housing is beveled.

18. A hemostatic valve assembly comprising:

A housing comprising a proximal end, a distal end, a housing side wall and a housing chamber between the proximal and distal ends, wherein at least a portion of the housing side wall tapers radially inwardly in a proximal to distal direction to form a continuously curved bowl shaped inner surface of the sidewall of the housing chamber;

a tubular sheath extending proximally from the housing and comprising a proximal end and a distal end and a sheath lumen extending there between;

a valve member having a continuously curved outer surface disposed at least partially within the housing chamber, the valve member comprising an open proximal end, a distal end having an orifice formed therein and an inner side wall extending between the proximal and distal ends of the valve member to form a valve cavity, the valve member being deformable between a closed configuration in which the orifice is substantially closed and an open configuration in which the orifice is open; and a biasing member disposed proximal to the valve member and moveable between a longitudinally compressed condition and a longitudinally expanded condition, wherein, when in the longitudinally expanded condition, the biasing member is configured to push the valve member longitudinally and against the continuously curved bowl shaped inner surface of the side wall of the housing, and wherein the continuously curved bowl shaped inner surface of the side wall of the housing is configured to urge at least the distal end of the valve member radially inwardly, thus urging the orifice to a substantially closed configuration, wherein the housing comprises an open aperture at its distal end such that an interventional device may be introduced proximally through the open aperture, advanced through the orifice, advanced through the housing chamber, and into the sheath, and wherein the orifice of the valve member is biased in the closed configuration and wherein when the orifice of the valve member is biased in the closed configuration, the open aperture is open.

19. The hemostatic valve assembly of claim 18 wherein the continuously curved outer surface of the valve member substantially corresponds to the continuously curved inner sidewall of the housing chamber.

20. The hemostatic valve assembly of claim 19, wherein the continuously curved outer surface of the valve member comprises a dome and the dome conforms to the continuously curved inner sidewall of the housing chamber.

21. A hemostatic valve assembly comprising:

a housing comprising a proximal end, a distal end and a side wall defining a housing chamber between the proximal and distal ends, wherein at least a portion of the housing side wall tapers radially inwardly in a proximal to distal direction to form a dome shaped inner surface;

a tubular sheath extending proximally from the housing and comprising a proximal end and a distal end and a sheath lumen extending therebetween;

a valve member disposed at least partially within the housing chamber, the valve member comprising an open proximal end, a distal end having an orifice formed therein, a valve cavity, and a dome shaped outer surface, the valve member being deformable between a closed configuration in which the orifice is substantially closed and an open configuration in which the orifice is open; and a biasing member disposed proximal to the valve member and moveable between a longitudinally compressed condition and a longitudinally expanded condition, wherein, when in the longitudinally expanded condition, the biasing member is configured to push the valve member longitudinally and against the tapered side wall of the housing, and wherein the dome shaped inner surface of the side wall of the housing is configured to urge at least the distal end of the valve member radially inwardly, thus urging the orifice to a substantially closed configuration, wherein the housing comprises an open aperture at its distal end such that an interventional device may be introduced proximally through the open aperture, advanced through the orifice, advanced through the housing chamber, and into the sheath, and wherein the orifice of the valve member is biased in the closed configuration and wherein when the orifice of the valve member is biased in the closed configuration, the open aperture is open.

22. The hemostatic valve assembly of claim 21, wherein the dome shaped outer surface of the valve member substantially conforms to the dome shaped inner surface of the housing.

* * * * *